United States Patent
Fujiwara et al.

(10) Patent No.: US 6,831,083 B2
(45) Date of Patent: Dec. 14, 2004

(54) PYRAZOLINE DERIVATIVE OR TETRAHYDROPYRIDAZINE DERIVATIVE AND MEDICINAL USE THEREOF

(75) Inventors: Junya Fujiwara, Mobara (JP); Kazuya Sakai, Mobara (JP); Kenji Kibayashi, Suita (JP); Fumiki Shimada, Chiba (JP); Yoshio Shiga, Mobara (JP); Shiro Takagi, Mobara (JP)

(73) Assignee: Mitsui Chemicals, Inc., Tokyo (JP)

( * ) Notice: Subject to any disclaimer, the term of this patent is extended or adjusted under 35 U.S.C. 154(b) by 104 days.

(21) Appl. No.: 10/239,311

(22) PCT Filed: Mar. 19, 2001

(86) PCT No.: PCT/JP01/02169
§ 371 (c)(1),
(2), (4) Date: Sep. 20, 2002

(87) PCT Pub. No.: WO01/70732
PCT Pub. Date: Sep. 27, 2001

(65) Prior Publication Data
US 2003/0149046 A1 Aug. 7, 2003

(30) Foreign Application Priority Data
Mar. 21, 2000 (JP) ........................................ 2000-078980

(51) Int. Cl.⁷ .................... C07D 401/06; C07D 401/14; C07D 403/06; A61K 31/4439; A61K 31/444
(52) U.S. Cl. ............... 514/252.03; 514/341; 546/275.4; 546/168; 544/238; 544/357; 544/405
(58) Field of Search ...................... 544/238; 546/275.4; 514/252.03, 341

(56) References Cited

FOREIGN PATENT DOCUMENTS

| JP | 1-226815 A | 9/1989 |
| JP | 11-292764 A | 10/1999 |

*Primary Examiner*—Mark L. Berch
*Assistant Examiner*—Kahsay Habte
(74) *Attorney, Agent, or Firm*—Burns, Doane, Swecker & Mathis, LLP

(57) ABSTRACT

Using a compound selected from compounds represented by the following formula (1)

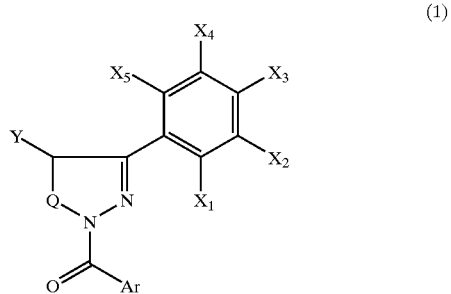

(which include 3-phenyl-2-pyrazoline derivatives and 3-phenyl-tetrahydropyridazine derivatives) and pharmacologically acceptable salts thereof, an agent is provided which can activate glutamic acid transporter and which is useful for prevention and/or treatment of cerebral ischemia (cerebral infarct and brain edema), amyotrophic lateral sclerosis (ALS), etc., all caused by glutamic acid toxicity.

9 Claims, No Drawings

PYRAZOLINE DERIVATIVE OR TETRAHYDROPYRIDAZINE DERIVATIVE AND MEDICINAL USE THEREOF

TECHNICAL FIELD

The present invention relates to a novel 3-phenyl-2-pyrazoline derivative or 3-phenyl-tetrahydropyridazine derivative, as well as to a pharmaceutically acceptable salt thereof. More particularly, the present invention relates to an agent containing the above compound, which can activate glutamic acid transporter and is useful for treatment and/or prevention of cerebral ischemia (cerebral infarct and brain edema), cephalotrauma, glaucoma, retinopathy, epilepsy and amyotrophic lateral sclerosis (ALS), all caused by glutamic acid toxicity.

BACKGROUND ART

Glutamic acid is an important excitatory neurotransmitter in the central nervous system and has a close connection with neuropathy caused during cerebral ischemia. There are reports on the excessive effusion of glutamic acid caused by ischemia in test animals, and also on persistent effusion of large amount of glutamic acid in the brain tissue of cerebral ischemia patient [B. Meldrum: Trends. Pharmacol. Sci. 1990, 11, 379–387]. Therefore, it is expected that brain tissue can be protected from cell death by controlling the excessive effusion of glutamic acid caused during ischemia.

Glutamic acid which effuses excessively into synapse gaps, is taken into cells by the action of glutamic acid transporter present in neurocytes or astrocytes, whereby an equilibrium is maintained. Up to now, five kinds of sodium-dependent glutamic acid transporters (GLT-1, GLAST, EAAC1, EAAT4 and EAAT5) have been cloned, and an active study has been made in recent years in order to make clear the functions thereof. It is considered that glutamic acid transporter is activated with an increase in the ectocytic concentration of glutamic acid, caused during ischemia and has an important role in protecting neurocytes from glutamic acid toxicity. Also, there is a report that the degeneration of glutamic acid transporter has a connection with neurodegeneration such as amyotrophic lateral sclerosis (ALS). Therefore, by activating glutamic acid transporter and removing the glutamic acid excessively effusing into synapse gaps, protective effects can be expected for various diseases considered to be caused by glutamic acid toxicity, such as cerebral ischemia (cerebral infarct and brain edema), sequela of cerebral ischemia, cephalotrauma, glaucoma, retinopathy, epilepsy, amyotrophic lateral sclerosis (ALS) and the like. However, there has heretofore been no report on any drug capable of activating glutamic acid transporter.

DISCLOSURE OF THE INVENTION

The object of the present invention is to provide a compound which can activate glutamic acid transporter and which is useful for prevention and/or treatment of cerebral ischemia (cerebral infarct and brain edema), sequela of cerebral ischemia, cephalotrauma, glaucoma, retinopathy, epilepsy and amyotrophic lateral sclerosis (ALS), all caused by glutamic acid toxicity; and a medicinal composition containing the compound.

The present inventors made a study to achieve the above object and found out that 3-phenyl-2-pyrazoline derivatives and 3-phenyl-tetahydropyridazine derivatives have an strong action for activating glutamic acid transporter. The present invention has been completed based on the finding.

The compound according to the present invention is a compound represented by the following formula (1) or a pharmacologically acceptable salt thereof:

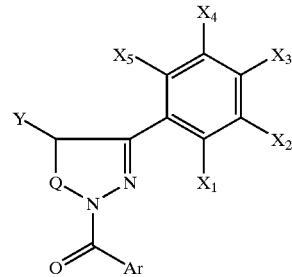

(1)

[wherein $X_1$, $X_2$, $X_3$, $X_4$ and $X_5$ may be the same or different and are each a hydrogen atom, an alkyl group of 1 to 6 carbon atoms, a trifluoromethyl group, a halogen atom, a nitro group, an alkyloxy group of 1 to 6 carbon atoms, an alkylthio group of 1 to 6 carbon atoms, an alkylsulfinyl group of 1 to 6 carbon atoms or an alkylsulfonyl group of 1 to 6 carbon atoms; Y is a hydrogen atom or an alkyl group of 1 to 4 carbon atoms; when $X_5$ is an alkyloxy group, an alkylthio group, an alkylsulfinyl group, an alkylsulfonyl group or an alkyl group, $X_5$ and Y may be bonded to ea other to form a 6- or 7-membered ring; Q is a methylene group or an ethylene group; and Ar is a 2-pyrazyl group, 3-quinolyl group or an unsubstituted or Rn-s bstituted 3-pyridyl group, each represented by one of the following formulas:

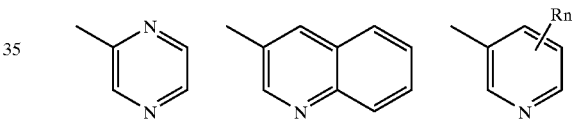

(R of Rn is an alkyl group of 1 to 6 carbon atoms or a halogen atom; n is an integer of 0 to 4; and Rn indicates that the number of R is n)].

The compound of the formula (1) includes 3-phenyl-2-pyrazoline derivatives and 3-phenyl-tetrahydropyridazine derivatives. The compound further includes pharmacologically acceptable salts of the compound of the formula (1).

Preferred forms of the compound of the formula (1) according to the present invention include the following compounds.

1. Compounds wherein Y is a hydrogen atom.
2. 3-Phenyl-2-pyrazoline derivatives wherein Q is a methylene group.
3. Compounds wherein Ar is a 3-pyridyl group.
4. Compounds wherein $X_5$ is an oxygen atom, Y is a methylene group, and $X_5$ and Y are bonded to each other to form a ring structure.
5. 3-Phenyl-2-pyrazoline derivatives where Y is a hydrogen atom and Q is a methylene group.
6. Compounds wherein $X_5$ is an oxygen atom, Y is a methylene group, $X_5$ and Y are bonded to each other to form a ring structure and Ar is 3-pyridyl group.

The process for producing the compound of the formula (1) according to the present invention comprises reacting a 3-phenyl-2-pyrazoline derivative or a 3-phenyl-tetrahydropyridazine derivative, both represented by the following formula (2):

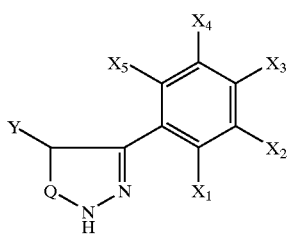

(2)

[wherein $X_1$, $X_2$, $X_3$, $X_4$, $X_5$, Y and Q have the same definitions as in the formula (1)] with a hetero ring derivative represented by the following formula (3):

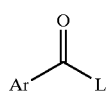

(3)

[wherein L is a hydroxyl group or an eliminatable group which can be easily substituted using a nucleophilic reagent; and Ar has the same definition as in the formula (1)].

The medicinal composition according to the present invention contains, as an active ingredient, a compound of the formula (1) or a pharmacologically acceptable salt thereof.

As medicinal applications of the medicinal composition, there can be mentioned pharmaceutical preparations used for treatment and/or prevention of cerebral ischemia (cerebral infarct and brain edema), sequela of cerebral ischemia, cephalotrauma, glaucoma, retinopathy, epilepsy and amyotrophic lateral sclerosis (ALS), all caused by glutamic acid toxicity in neurocytes.

BEST MODE FOR CARRYING OUT THE INVENTION

The present invention is described in detail below.

First, description is made on the substituents in the formula (1).

The alkyl group of 1 to 6 carbon atoms refers to a straight chain, branched chain or cyclic alkyl group of 1 to 6 carbon atoms and can be exemplified by methyl group, ethyl group, n-propyl group, n-butyl group, n-pentyl group, n-hexyl group, isopropyl group, cyclopropyl group, 2-methylpropyl group, 1-methylpropyl group, tert-butyl group, cyclobutyl group, cyclopentyl group, 3-methylbutyl group, 2-methylbutyl group, 1-methylbutyl group, 1,1-dimethylpropyl group, 1,2-dimethylpropyl group, 2,2-dimethylpropyl group, cyclohexyl group, 4-methylpentyl group, 3-methylpentyl group, 2-methylpentyl group, 1-methylpentyl group, 1,2,2-trimethylpropyl group, 1,1,2-trimethylpropyloxy group, 1,1-dimethylbutyloxy group, 2,2-dimethylbutyloxy group, 1,3-dimethylbutyloxy group and 2,3-dimethylbutyloxy group.

The halogen atom can be exemplified by iodine atom, bromine atom, chlorine atom and fluorine atom.

The alkyloxy group of 1 to 6 carbon atoms refers to a straight chain, branched chain or cyclic alkyloxy group of 1 to 6 carbon atoms and can be exemplified by methoxy group, ethoxy group, n-propyloxy group, n-butyloxy group, n-pentyloxy group, n-hexyloxy group, isopropyloxy group, tert-butyloxy group, cyclopropyloxy group, cyclobutyloxy group, cyclopentyloxy group and cyclohexyloxy group.

The alkylthio group of 1 to 6 carbon atoms refers to a straight chain, branched chain or cyclic alkylthio group of 1 to 6 carbon atoms and can be exemplified by methylthio group, ethylthio group, n-propylthio group, n-butylthio group, n-pentylthio group, n-hexylthio group, isopropylthio group, tert-butylthio group, cyclopropylthio group, cyclobutylthio group, cyclopentylthio group and cyclohexylthio group.

The alkylsulfinyl group of 1 to 6 carbon atoms refers to a straight chain, branched chain or cyclic alkylsulfinyl group of 1 to 6 carbon atoms and can be exemplified by methylsulfinyl group, ethylsulfinyl group, n-propylsulfinyl group, n-butylsulfinyl group, n-pentylsulfinyl group, n-hexylsulfinyl group, isopropylsulfinyl group, tert-butylsulfinyl group, cyclopropylsulfinyl group, cyclobutylsulfinyl group, cyclopentylsulfinyl group and cyclohexylsulfinyl group.

The alkylsulfonyl group of 1 to 6 carbon atoms refers to a straight chain, branched chain or cyclic alkylsulfonyl group of 1 to 6 carbon atoms and can be exemplified by methylsulfonyl group, ethylsulfonyl group, n-propylsulfonyl group, n-butylsulfonyl group, n-pentylsulfonyl group, n-hexylsulfonyl group, isopropylsulfonyl group, tert-butylsulfonyl group, cyclopropylsulfonyl group, cyclobutylsulfonyl group, cyclopentylsulfonyl group and cyclohexylsulfonyl group.

In the formula (1), the alkyl group of 1 to 4 carbon atoms represented by Y refers to a straight chain, branched chain or cyclic alkyl group of 1 to 4 carbon atoms and can be exemplified by methyl group, ethyl group, n-propyl group, n-butyl group, isopropyl group, cyclopropyl group, tert-butyl group and cyclobutyl group.

The alkyl group of 1 to 6 carbon atoms as a substituent Rn when Ar is a 3-pyridyl group, refers to a straight chain, branched chain or cyclic alkyl group of 1 to 6 carbon atoms and can be exemplified by methyl group, ethyl group, n-propyl group, n-butyl group, n-pentyl group, n-hexyl group, isopropyl group, cyclopropyl group, tert-butyl group, cyclobutyl group, cyclopentyl group and cyclohexyl group. The halogen atom can be exemplified by iodine atom, bromine atom, chlorine atom and fluorine atom.

In the compound represented by the formula (1) according to the present invention, when the compound has an asymmetric carbon atom in the molecule, all of the optical isomers of R- and S-configurations based on the asymmetric carbon atom are included in the present invention.

The compound of the formula (1) can be converted into a pharmacologically acceptable salt thereof as necessary. As the salt, there can be mentioned, for example, salts with inorganic acids such as hydrochloric acid, hydrobromic acid, phosphoric acid, sulfuric acid and the like; and salts with organic acids such as formic acid, acetic acid, fumaric acid, citric acid, maleic acid, oxalic acid, malic acid, tartaric acid, methanesulfonic acid, benzenesulfonic acid, p-toluenesulfonic acid and the like.

Next, the process for producing the compound of the present invention is described in detail below. The compound of the present invention can be synthesized, for example, by reacting a 3-phenyl-2-pyrazoline derivative or 3-phenyl-tetrahydropyridazine derivative represented by the following formula (2) and a hetero ring derivative represented by the following formula (3):

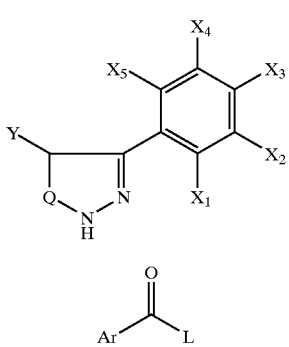

by mixing them without any solvent or in a state that they are dissolved or suspended in an appropriate solvent or dispersing agent.

There is no particular restriction as to the proportions of the formula (2) and (3) used. However, the molar ratio of the former and the latter is ordinarily 20:1 to 1:20, preferably 1:1 to 10:1. The compound obtained by the present reaction can be further purified by an ordinary method such as recrystallization, silica gel chromatography or the like.

The reaction is explained below on a case that L is a hydroxyl group and on a case that L is other than hydroxyl group.

(1) Case that L is a Hydroxyl Group

A condensation agent can be used in the reaction. As the solvent for the condensation agent appropriately used in the reaction, there can be mentioned, for example, benzene, toluene, xylene, 1,4-dioxane, dimethylformamide (hereinafter referred to as DMF), tetrahydrofuran (hereinafter referred to as THF), ethyl ether, 1,2-dimethoxyethane, dimethyl sulfoxide (hereinafter referred to as DMSO), chloroform, dichloromethane and 1,2-dichloroethane.

As the condensation agent usable in the reaction, there can be mentioned, for example, 1,1'-carbonyldiimidazole [H. A. Staab: Angew. Chem. Int. Ed. Engl., 1, 351–367, (1962)], dicyclohexylcarbodiimide (hereinafter referred to as DCC), 1-ethyl-3-(3'-dimethylaminopropyl)carbodiimide and diphenylphosphoryl azide.

The reaction is conducted at a temperature ranging from room temperature to the refluxing temperature of the reaction mixture. The reaction is conducted, for example, at −10 to 150° C., preferably at room temperature to 100° C. The reaction time is about 1 to 48 hours although it varies depending upon the reaction conditions used.

(2) Case that L is Other than Hydroxyl Group

As the activated form of the hetero ring derivative represented by the formula (3), there can be mentioned, for example, an acid halide (a case that L is a halogen atom) and an acid anhydride (a case that L is an alkoxycarbonyloxy group; and they can be easily synthesized from a carboxylic acid of the formula (3) (a case that L is OH), by a known method.

As to the acid halide, a carboxylic acid chloride can be synthesized from a carboxylic acid using, for example, a chlorinating agent such as thionyl chloride, oxazlyl chloride, phosphorus pentachloride or the like.

The acid anhydride can be synthesized from a carboxylic acid using, for example, a monoalkyl carbonate (e.g. ethyl chlorocarbonate) and a base (e.g. triethylamine).

As the solvent or dispersing agent appropriately used in the reaction between the activated form of the above carboxylic acid compound and a 3-phenyl-2-pyrazoline derivative or 3-phenyl-tetrahydropyridazine derivative, there can be mentioned, for example, methyl ethyl ketone, 1,4-dioxane, DMF, THF, ethyl ether, 1,2-dimethoxyethane, dimethyl sulfoxide, benzene, xylene, toluene, chloroform, dichloromethane, 1,2-dichloroethane, pyridine, and, optionally, alcohols such as methanol, ethanol, isopropanol and the like.

The reaction between 3-substituted phenyl-2-pyrazoline derivative or 3-phenyl-tetrahydropyridazine derivative and the activated form of the carboxylic acid compound is conducted at a temperature ranging from room temperature to the refluxing temperature of the reaction mixture, for example, from −10 to 150° C., preferably 0 to 100° C. The reaction time is about 1 to 48 hours although it varies depending upon the reaction conditions employed. As the base used for accelerating the reaction, there can be mentioned, for example, organic bases such as pyridine, dimethylaminopyridine, triethylamine, diisopropylethylamine and the like; and inorganic bases such as potassium carbonate, sodium carbonate, sodium hydroxide, potassium hydroxide and the like.

The 3-phenyl-2-pyrazoline derivative and 3-phenyl-tetrahydropyridazine derivative, represented by the formula (2) can be synthesized by the following known processes.

[Synthesis Process 1] When Q of the Formula (2) is Methylene Group

For example, 3-phenyl-1,4,5,6-tetrahydropyridazine can be synthesized by reducing 3-phenyl-1,4,5,6-tetrahydropyridazine-6-one [synthesized according to F. J. McEvoy: J. Med. Chem., 17, 281–286 (1974)] according to J. L. Aubagnac: Bull. Chem. Soc. Fr. 2859–2868 (1972).

[Synthesis Process 2] When Q of Formula (2) is Ethylene Group

For example, a β-dialkylaminopropiophenone derivative synthesized from an acetophenone derivative according to the method described in C. E. Maxwell: Org. Synth. Coll. Vol. III, 305–306 can be converted into a 3-phenylpyrazoline derivative according to the method described in A. N. Kost: Journal of General Chemistry of USSR, 27, 1155–1158 (1957).

As the compounds included in the formula (1) of the present invention, there can be mentioned, for example, the following specific compounds. However, the present invention is not restricted thereto.

(1) 1-(2-Pyrazinoyl)-3-phenyl-1,4,5,6-tetrahydropyridazine
(2) 1-Nicotinoyl-3-phenyl-1,4,5,6-tetrahydropyridazine
(3) 1-(2-Methylnicotinoyl)-3-phenyl-1,4,5,6-tetrahydropyridazine
(4) 1-(4-Methylnicotinoyl)-3-phenyl-1,4,5,6-tetrahydropyridazine
(5) 1-(5-Methylnicotinoyl)-3-phenyl-1,4,5,6-tetrahydropyridazine
(6) 1-(6-Methylnicotinoyl)-3-phenyl-1,4,5,6-tetrahydropyridazine
(7) 1-(2-Iodonicotinoyl)-3-phenyl-1,4,5,6-tetrahydropyridazine
(8) 1-(4-Bromonicotinoyl)-3-phenyl-1,4,5,6-tetrahydropyridazine
(9) 1-(5-Chloronicotinoyl)-3-phenyl-1,4,5,6-tetrahydropyridazine
(10) 1-(6-Fluoronicotinoyl)-3-phenyl-1,4,5,6-tetrahydropyridazine
(11) 1-(3-Quinolylcarbonyl)-3-phenyl-1,4,5,6-tetrahydropyridazine
(12) 1-(2-pyrazinoyl)-3-phenyl-2-pyrazoline
(13) 1-Nicotinoyl-3-phenyl-2-pyrazoline
(14) 1-(2-Methylnicotinoyl)-3-phenyl-2-pyrazoline

(15) 1-(4-Ethylnicotinoyl)-3-phenyl-2-pyrazoline
(16) 1-(5-n-Propylnicotinoyl)-3-phenyl-2-pyrazoline
(17) 1-(2-n-Butylnicotinoyl)-3-phenyl-2-pyrazoline
(18) 1-(4-n-Pentylnicotinoyl)-3-phenyl-2-pyrazoline
(19) 1-(5-n-Hexylnicotinoyl)-3-phenyl-2-pyrazoline
(20) 1-(6-Methylnicotinoyl)-3-phenyl-2-pyrazoline
(21) 1-(2-Iodonicotinoyl)-3-phenyl-2-pyrazoline
(22) 1-(4-Chloronicotinoyl)-3-phenyl-2-pyrazoline
(23) 1-(5-Bromonicotinoyl)-3-phenyl-2-pyrazoline
(24) 1-(6-Fluoronicotinoyl)-3-phenyl-2-pyrazoline
(25) 1-(3-Quinolylcarbonyl)-3-phenyl-pyrazoline
(26) 1-(2-Pyrazinoyl)-3-phenyl-4-methyl-1,4,5,6-tetrahydropyridazine
(27) 1-Nicotinoyl-3-phenyl-4-methyl-1,4,5,6-tetrahydropyridazine
(28) 1-Nicotinoyl-3-phenyl-4-ethyl-1,4,5,6-tetrahydropyridazine
(29) 1-Nicotinoyl-3-phenyl-4-isopropyl-1,4,5,6-tetrahydropyridazine
(30) 1-Nicotinoyl-3-phenyl-4-tert-butyl-1,4,5,6-tetrahydropyridazine
(31) 1-(2-pyrazinoyl)-3-phenyl-4-methyl-2-pyrazoline
(32) 1-Nicotinoyl-3-phenyl-4-ethyl-2-pyrazoline
(33) 1-Nicotinoyl-3-phenyl-4-cyclopropyl-2-pyrazoline
(34) 1-Nicotinoyl-3-phenyl-4-isobutyl-2-pyrazoline
(35) 1-Nicotinoyl-3-(6-iodophenyl)-2-pyrazoline
(36) 1-Nicotinoyl-3-(5-bromophenyl)-2-pyrazoline
(37) 1-Nicotinoyl-3-(4-fluorophenyl)-2-pyrazoline
(38) 1-Nicotinoyl-3-(4-bromophenyl)-2-pyrazoline
(39) 1-Nicotinoyl-3-(4-chlorophenyl)-2-pyrazoline
(40) 1-Nicotinoyl-3-(3-chlorophenyl)-2-pyrazoline
(41) 1-Nicotinoyl-3-(2-fluorophenyl)-2-pyrazoline
(42) 1-Nicotinoyl-3-(2-chlorophenyl)-2-pyrazoline
(43) 1-(2-Pyrazinoyl)-3-(4-bromophenyl)-2-pyrazoline
(44) 1-(3-Quinolylcarbonyl)-3-(4-chlorophenyl)-2-pyrazoline
(45) 1-Nicotinoyl-3-(4-chlorophenyl)-1,4,5,6-tetrahydropyridazine
(46) 1-(2-Pyrazinoyl)-3-(3-bromophenyl)-1,4,5,6-tetrahydropyridazine
(47) 1-(3-Quinolylcarbonyl)-3-(2-fluorophenyl)-1,4,5,6-tetrahydropyridazine
(48) 1-Nicotinoyl-3-(6-ethoxyphenyl)-2-pyrazoline
(49) 1-Nicotinoyl-3-(5-n-propyloxyphenyl)-2-pyrazoline
(50) 1-Nicotinoyl-3-(5-n-hexyloxyphenyl)-2-pyrazoline
(51) 1-Nicotinoyl-3-(4-methoxyphenyl)-2-pyrazoline
(52) 1-Nicotinoyl-3-(4-ethoxyphenyl)-2-pyrazoline
(53) 1-Nicotinoyl-3-(4-n-butyloxyphenyl)-2-pyrazoline
(54) 1-Nicotinoyl-3-(4-n-hexyloxyphenyl)-2-pyrazoline
(55) 1-Nicotinoyl-3-(3-isobutyloxyphenyl)-2-pyrazoline
(56) 1-Nicotinoyl-3-(3-n-pentyloxyphenyl)-2-pyrazoline
(57) 1-Nicotinoyl-3-(2-methoxyphenyl)-2-pyrazoline
(58) 1-Nicotinoyl-3-(2-ethoxyphenyl)-2-pyrazoline
(59) 1-Nicotinoyl-3-(2,4-di-methoxyphenyl)-2-pyrazoline
(60) 1-Nicotinoyl-3-(2-methoxyphenyl)-4-methyl-2-pyrazoline
(61) 1-(2-Pyrazinoyl)-3-(4-methoxyphenyl)-2-pyrazoline
(62) 1-(3-Quinolylcarbonyl)-3-(2-methoxyphenyl)-2-pyrazoline
(63) 1-Nicotinoyl-3-(4-methoxyphenyl)-1,4,5,6-tetrahydropyridazine
(64) 1-Nicotinoyl-3-(6-isopropylphenyl)-2-pyrazoline
(65) 1-Nicotinoyl-3-(5-ethylphenyl)-2-pyrazoline
(66) 1-Nicotinoyl-3-(5-methylphenyl)-2-pyrazoline
(67) 1-Nicotinoyl-3-(4-isobutylphenyl)-2-pyrazoline
(68) 1-Nicotinoyl-3-(4-n-propylphenyl)-2-pyrazoline
(69) 1-Nicotinoyl-3-(3-methylphenyl)-2-pyrazoline
(70) 1-Nicotinoyl-3-(2-methylphenyl)-2-pyrazoline
(71) 1-Nicotinoyl-3-(2-n-pentylphenyl)-2-pyrazoline
(72) 1-Nicotinoyl-3-(2-cyclohexylphenyl)-2-pyrazoline
(73) 1-Nicotinoyl-3-(2,4-dimethylphenyl)-2-pyrazoline
(74) 1-(2-Pyrazinoyl)-3-(4-methylphenyl)-2-pyrazoline
(75) 1-(3-Quinolylcarbonyl)-3-(3-methylphenyl)-2-pyrazoline
(76) 1-Nicotinoyl-3-(2-methylphenyl)-1,4,5,6-tetrahydropyridazine
(77) 1-Nicotinoyl-3-(4-trifluoromethylphenyl)-2-pyrazoline
(78) 1-Nicotinoyl-3-(3-trifluoromethylphenyl)-2-pyrazoline
(79) 1-Nicotinoyl-3-(2-trifluoromethylphenyl)-2-pyrazoline
(80) 1-(3-Quinolylcarbonyl)-3-(4-trifluoromethylphenyl)-2-pyrazoline
(81) 1-(3-Quinolylcarbonyl)-3-(3-trifluoromethylphenyl)-2-pyrazoline
(82) 1-Nicotinoyl-3-(2-trifluoromethylphenyl)-1,4,5,6-tetrahydropyridazine
(83) 1-Nicotinoyl-3-(6-nitrophenyl)-2-pyrazoline
(84) 1-Nicotinoyl-3-(5-nitrophenyl)-2-pyrazoline
(85) 1-Nicotinoyl-3-(4-nitrophenyl)-2-pyrazoline
(86) 1-Nicotinoyl-3-(3-nitrophenyl)-2-pyrazoline
(87) 1-Nicotinoyl-3-(2-nitrophenyl)-2-pyrazoline
(88) 1-(2-Pyrazinoyl)-3-(4-nitrophenyl)-2-pyrazoline
(89) 1-(3-Quinolylcarbonyl)-3-(4-nitrophenyl)-2-pyrazoline
(90) 1-Nicotinoyl-3-(2-nitrophenyl)-1,4,5,6-tetrahydropyridazine
(91) 1-Nicotinoyl-3-(6-methylthiophenyl)-2-pyrazoline
(92) 1-Nicotinoyl-3-(5-ethylthiophenyl)-2-pyrazoline
(93) 1-Nicotinoyl-3-(4-n-propylthiophenyl)-2-pyrazoline
(94) 1-Nicotinoyl-3-(3-n-butylthiophenyl)-2-pyrazoline
(95) 1-Nicotinoyl-3-(2-n-pentylthiophenyl)-2-pyrazoline
(96) 1-Nicotinoyl-3-(4-n-hexylthiophenyl)-2-pyrazoline
(97) 1-(2-Pyrazinoyl)-3-(3-ethylphenyl)-2-pyrazoline
(98) 1-(3-Quinolylcarbonyl)-3-(2-methylthiophenyl)-2-pyrazoline
(99) 1-Nicotinoyl-3-(2-methylthiophenyl)-1,4,5,6-tetrahydropyridazine
(100) 1-Nicotinoyl-3-(6-methylsulfinylphenyl)-2-pyrazoline
(101) 1-Nicotinoyl-3-(5-ethylsulfinylphenyl)-2-pyrazoline
(102) 1-Nicotinoyl-3-(4-isopropylsulfinylphenyl)-2-pyrazoline
(103) 1-Nicotinoyl-3-(3-isobutylsulfinylphenyl)-2-pyrazoline
(104) 1-Nicotinoyl-3-(2-cyclopentylsulfinylphenyl)-2-pyrazoline
(105) 1-Nicotinoyl-3-(4-n-hexylsulfinylphenyl)-2-pyrazoline
(106) 1-(2-Pyrazinoyl)-3-(3-methylsulfinylphenyl)-2-pyrazoline
(107) 1-(3-Quinolylcarbonyl)-3-(2-methylsulfinylphenyl)-2-pyrazoline
(108) 1-Nicotinoyl-3-(2-ethylsulfinylphenyl)-1,4,5,6-tetrahydropyridazine
(109) 1-Nicotinoyl-3-(6-ethylsulfonylphenyl)-2-pyrazoline
(110) 1-Nicotinoyl-3-(5-methylsulfonylphenyl)-2-pyrazoline
(111) 1-Nicotinoyl-3-(4-cyclopropylsulfonylphenyl)-2-pyrazoline
(112) 1-Nicotinoyl-3-(3-cyclobutylsulfonylphenyl)-2-pyrazoline
(113) 1-Nicotinoyl-3-(2-n-pentylsulfonylphenyl)-2-pyrazoline
(114) 1-Nicotinoyl-3-(4-n-hexylsulfonylphenyl)-2-pyrazoline
(115) 1-(2-Pyrazinoyl)-3-(3-methylsulfonylphenyl)-2-pyrazoline (116) 1-(3-Quinolylcarbonyl)-3-(2-methylsulfonylphenyl)-2-pyrazoline
(117) 1-Nicotinoyl-3-(4-methylsulfonylphenyl)-1,4,5,6-tetrahydropyridazine
(118) 2-Nicotinoyl-3,3a-dihydro-2H,4H-[1]benzopyrano[4,3-c]pyrazole
(119) 2-(2-Pyrazinoyl)-3,3a-dihydro-2H,4H-[1]benzopyrano[4,3-c]pyrazole
(120) 2-(3-Quinolylcarbonyl)-3,3a-dihydro-2H,4H-[1]benzopyrano[4,3-c]pyrazole
(121) 2-Nicotinoyl-6-methoxy-3,3a-dihydro-2H,4H-[1]benzopyrano[4,3-c]pyrazole
(122) 2-Nicotinoyl-6-ethoxy-3,3a-dihydro-2H,4H-[1]benzopyrano[4,3-c]pyrazole
(123) 2-Nicotinoyl-7-methoxy-3,3a-dihydro-2H,4H-[1]benzopyrano[4,3-c]pyrazole
(124) 2-Nicotinoyl-7-n-propyloxy-3,3a-dihydro-2H,4H-[1]benzopyrano[4,3-c]pyrazole
(125) 2-Nicotinoyl-8-methoxy-3,3a-dihydro-2H,4H-[1]-benzopyrano[4,3-c]pyrazole
(126) 2-Nicotinoyl-8-n-butyloxy-3,3a-dihydro-2H,4H-[1]-benzopyrano[4,3-c]pyrazole
(127) 2-Nicotinoyl-6-chloro-3,3a-dihydro-2H,4H-[1]-benzopyrano[4,3-c]pyrazole
(128) 2-Nicotinoyl-6-iodo-3,3a-dihydro-2H,4H-[1]-benzopyrano[4,3-c]pyrazole
(129) 2-Nicotinoyl-7-chloro-3,3a-dihydro-2H,4H-[1]-benzopyrano[4,3-c]pyrazole
(130) 2-Nicotinoyl-7-bromo-3,3a-dihydro-2H,4H-[1]-benzopyrano[4,3-c]pyrazole
(131) 2-Nicotinoyl-8-chloro-3,3a-dihydro-2H,4H-[1]-benzopyrano[4,3-c]pyrazole
(132) 2-Nicotinoyl-8-fluoro-3,3a-dihydro-2H,4H-[1]-benzopyrano[4,3-c]pyrazole
(133) 2-Nicotinoyl-6-methyl-3,3a-dihydro-2H,4H-[1]-benzopyrano[4,3-c]pyrazole
(134) 2-Nicotinoyl-6-ethyl-3,3a-dihydro-2H,4H-[1]-benzopyrano[4,3-c]pyrazole
(135) 2-Nicotinoyl-7-methyl-3,3a-dihydro-2H,4H-[1]-benzopyrano[4,3-c]pyrazole
(136) 2-Nicotinoyl-7-isopropyl-3,3a-dihydro-2H,4H-[1]-benzopyrano[4,3-c]pyrazole
(137) 2-Nicotinoyl-8-methyl-3,3a-dihydro-2H,4H-[1]-benzopyrano[4,3-c]pyrazole
(138) 2-Nicotinoyl-8-tert-butyl-3,3a-dihydro-2H,4H-[1]-benzopyrano[4,3-c]pyrazole
(139) 2-Nicotinoyl-3,3a-dihydro-2H,4H-[1]-benzothiopyrano[4,3-c]pyrazole
(140) 2-(2-Pyrazinoyl)-3,3a-dihydro-2H,4H-[1]-benzothiopyrano[4,3-c]pyrazole
(141) 2-(3-Quinoylcarbonyl)-3,3a-dihydro-2H,4H-[1]-benzothiopyrano[4,3-c]pyrazole
(142) 2-Nicotinoyl-3,3a-dihydro-2H,4H-[1]-benzothiopyrano[4,3-c]pyrazole-S-oxide
(143) 2-(2-Pyrazinoyl)-3,3a-dihydro-2H,4H-[1]-benzothiopyrano[4,3-c]pyrazole-S-oxide
(144) 2-(3-Quinolylcarbonyl)-3,3a-dihydro-2H,4H-[1]-benzothiopyrano[4,3-c]pyrazole-S-oxide
(145) 2-Nicotinoyl-3,3a-dihydro-2H,4H-[1]-benzothiopyrano[4,3-c]pyrazole-S-dioxide
(146) 2-(2-Pyrazinoyl)-3,3a-dihydro-2H,4H-[1]-benzothiopyrano[4,3-c]pyrazole-S-dioxide
(147) 2-(3-Quinolylcarbonyl)-3,3a-dihydro-2H,4H-[1]-benzothiopyrano[4,3-c]pyrazole-S-dioxide
(148) 2-Nicotinoyl-2,3a,4,5-tetrahydronaphtho[1,2-c]pyrazole
(149) 2-(2-Pyrazinoyl)-2,3a,4,5-tetrahydronaphtho[1,2-c]pyrazole
(150) 2-(3-Quinolylcarbonyl)-2,3a,4,5-tetrahydronaphtho[1,2-c]pyrazole Pharmaceutical preparations can be obtained by a known method. As the form thereof, various forms can be selected so as to meet the purpose of treatment. As representative forms, there can be mentioned a solid agent, a liquid agent, a suppository, etc. More particularly, there are the following agents. That is, the solid agent includes tablets, pills, a powder, granules, capsules, etc.; the liquid agent includes an injection (a solution), a suspension, a syrup, an emulsion, etc.; and the other agent includes a suppository, etc.

In forming tablets, there can be widely used, as the carrier, various materials heretofore known well in the field. Examples thereof are excipients such as lactose, sucrose, sodium chloride, glucose, urea, starch, calcium carbonate, kaolin, crystalline cellulose, silicic acid and the like; binders such as water, ethanol, propanol, simple syrup, glucose solution, starch solution, gelatin solution, shellac solution, methyl cellulose solution, hydroxypropyl cellulose solution, polyvinylpyrrolidone solution, carboxymethyl cellulose solution and the like; disintegrators such as dry starch, sodium alginate, agar powder, sodium hydrogencarbonate, calcium carbonate, polyoxyethylene sorbitan/fatty acid ester, sodium lauryl sulfate, stearic acid glyceride, starch, glucose and the like; disintegration inhibitors such as sucrose, stearic acid, cacao butter, hydrogenated oil and the like; absorption accelerators such as quaternary ammonium base, sodium lauryl sulfate and the like; humectants such as glycerine, starch and the like; adsorbents such as starch, lactose, kaolin, bentonite, colloidal silicic acid, crystalline cellulose, light silicic acid anhydride and the like; and lubricants such as talc, stearic acid salt, boric acid powder, polyethylene glycol and the like.

As necessary, the tablets can be formed in the form of ordinary coated tablets, for example, sugar-coated tablets, gelatin-coated tablets, enteric-coated tablets or film-coated tablets; or in the form of double-layered tablets or multi-layered tablets.

In forming pills, there can be widely used, as the carrier, materials heretofore known in the field. Examples thereof are excipients such as glucose, lactose, starch, cacao butter, hardened vegetable oil, kaolin, talc and the like; binders such as powdered acacia, powdered tragacanth, gelatin and the like; and disintegrators such as calcium calmerose, agar and the like.

Capsules can be prepared generally by mixing an active ingredient compound with the above mentioned carrier and filling the mixture in a hard gelatin capsule, a soft capsule or the like, according to an ordinary method.

In preparing an injection in the form of a liquid agent, an emulsion or a suspension, there can be used, as the diluent, various materials generally used in the field, for example, water, ethanol, macrogol, propylene glycol, ethoxylated isostearyl alcohol, polyoxylated isostearyl alcohol, polyoxyethylene sorbitan/fatty acid ester, cotton seed oil, corn oil, peanut oil and olive oil. It is possible to add water to a compound of the present invention and further add an appropriate surfactant to prepare an aqueous suspension, or add a surfactant such as polyoxyethylene hardened castor oil (HCO-60), Polysorbate 80, polyethylene glycol or the like to prepare an emulsion. In the pharmaceutical preparation may be added sodium chloride, glucose or glycerine. There may also be added an ordinary solubilizer, a buffer agent, a soothing agent, etc.

In preparing a suppository, there can be widely used, as the carrier, various materials known heretofore. Examples thereof are a polyethylene glycol, cacao butter, a higher alcohol, a higher alcohol ester, gelatin and semi-synthetic glyceride.

These pharmaceutical preparations may further contain, as necessary, a coloring agent, a preservative, a perfume, a flavoring agent, a sweetening agent, etc. and, moreover, other medicine.

There is no particular restriction as to the method for administering the above pharmaceutical preparations of the present invention. They are administered in methods matching the form of each preparation, the age, sex and other conditions of patient, and the degree of disease. For example, tablets, pills, a liquid agent, a suspension, an emulsion, a powder, granules, a syrup and capsules are administered orally; an injection is administered intravenously as it is or by being mixed with an ordinary auxiliary solution such as glucose, amino acid or the like, or, as necessary, is administered intramuscularly, subcutaneously or intraperitoneally; and a suppository is administered intrarectally.

The dosages of these pharmaceutical preparations are appropriately selected depending upon the usage, the age, sex and other conditions of patient and the degree of disease. However, the dosage is ordinarily such that the amount of active ingredient compound administered is about 0.001 to 1,000 mg per day per adult. It is desired that each unit form administered contains about 0.001 to 1,000 mg of an active ingredient compound.

Reference Examples, Examples, Preparation Examples and Test Examples of the present invention are described below. However, the present invention is not restricted thereto.

REFERENCE EXAMPLE 1

Synthesis of 3-phenyl-1,4,5,6-tetrahydropyridazine

3-Phenyl-1,4,5,6-tetrahydropyridazinone (3.0 g) was dissolved in THF (100 ml). Thereto was added lithium aluminum hydride (0.5 g) at room temperature. The mixture was stirred for 3 hours. To the reaction mixture were added ethyl acetate, ethanol and water in this order. The resulting insolubles were removed by filtration. The filtrate was concentrated to obtain 2.4 g of a title compound as crystals.

REFERENCE EXAMPLE 2

Synthesis of 3-phenyl-2-pyrazoline

Hydrazine monohydrate (6.2 g) was dissolved in ethanol (12 ml). Thereto was dropwise added a solution of 3-(N,N-dimethylamino)propiophenone (5.4 g) dissolved in ethanol (10 ml) in a nitrogen atmosphere at room temperature. The resulting mixture was refluxed for 3 hours with heating. The reaction mixture was poured into ice water. Extraction with chloroform was conducted, followed by drying and concentration, to obtain 4 g of a title compound.

REFERENCE EXAMPLE 3

Synthesis of 3,3a-dihydro-2H,4H-[1]-benzopyrano[4,3-c]pyrazole

Hydrazine monohydrate (7.2 g) was dissolved in ethanol (10 ml). Thereto was dropwise added a solution of 3-(N,N-dimethylaminomethyl)-4-chromanone (6.7 g) dissolved in ethanol (10 ml) in a nitrogen atmosphere at room temperature. The resulting mixture was refluxed for 4 hours with heating. The reaction mixture was poured into ice water. Extraction with chloroform was conducted, followed by drying and concentration, to obtain 6 g of a title compound.

EXAMPLE 1

Synthesis of 1-nicotinoyl-3-phenyl-1,4,5,6-tetrahydropyridazine

3-Phenyl-1,4,5,6-tetrahydropyridazine (2.4 g) synthesized in Reference Example 1 was dissolved in chloroform (50 ml). Thereto were added nicotinic acid chloride hydrochloride (2.6 g) and triethylamine (3.2 g) with ice-cooling. Stirring was conducted for 30 minutes. The reaction mixture was washed with water, dried over anhydrous sodium sulfate and then concentrated. The residue was purified by silica gel column chromatography to obtain 1.8 g of a title compound.

Melting point: 84 to 86° C.

$^1$H-NMR (CDCl$_3$) δ ppm: 2.15 (t, 2H), 2.73 (t, 2H), 4.03 (t, 2H), 7.33–7.40 (m, 4H), 7.57–7.59 (m, 2H), 8.06–8.09 (m, 1H), 8.68–8.69 (m, 1H), 9.02 (d, 1H).

EXAMPLE 2

Synthesis of 1-(2-Pyrazinoyl)-3-phenyl-1,4,5,6-tetrahydropyridazine

3-Phenyl-1,4,5,6-tetrahydropyridazine (2.9 g) was used as a starting material; 2-pyrazinolyl chloride was used in place of nicotinic acid chloride hydrochloride; and the same operation as in Example 1 was conducted to obtain 1.5 g of a title compound.

Melting point: 98 to 100° C.

$^1$H-NMR(CDCl$_3$), δ ppm: 2.0–2.3 (m, 2H), 2.6–2.8 (m, 2H), 4.0–4.2 (m, 2H), 7.2–7.6 (m, 5H), 8.6–9.0 (m, 3H).

EXAMPLE 3

Synthesis of 1-nicotinoyl-3-phenyl-2-pyrazoline

3-Phenyl-2-pyrazoline (2.9 g) synthesized in Reference Example 2 was dissolved in chloroform (20 ml). Thereto were added nicotinic acid chloride hydrochloride (4 g) and triethylamine (6 ml) with ice-cooling. Stirring was conducted for 30 minutes at room temperature. The reaction mixture was washed with water and concentrated under vacuum. The residue was purified by silica gel column chromatography (methanol:chloroform=1/100) to obtain 3.7 g of a title compound.

Melting point: 87 to 89° C.

$^1$H-NMR(DMSO-d$_6$), δ ppm : 3.37 (t, 2H), 4.16 (t, 2H), 7.45–7.55 (m, 4H), 7.68–7.73 (m, 2H), 8.21–8.26 (m, 1H), 8.30–8.71 (m, 1H), 9.02 (d, 1H).

EXAMPLE 4

Synthesis of 1-nicotinoyl-3-phenyl-2-pyrazoline hydrochloride

1-Nicotinoyl-3-phenyl-2-pyrazoline (0.1 g) synthesized in Example 3 was dissolved in ethanol (5 ml). Thereto was added 1 N hydrochloric acid-ethanol (0.9 ml) with ice-cooling. The resulting crystals were collected by filtration, washed with ether and dried to obtain 0.1 g of a title compound as yellow crystals.

Melting point: 235 to 238° C.

$^1$H-NMR(DMSO-d$_6$) δ ppm : 3.41 (t, 2H), 4.18 (t, 2H), 7.44–7.54 (m, 3H), 7.71–7.78 (m, 2H), 7.94–7.99 (m, 1H), 8.70–8.74 (m, 1H), 8.74–8.95 (m, 1H), 9.24 (d, 1H).

EXAMPLE 5

Synthesis of 1-nicotinoyl-3-phenyl-2-pyrazoline methanesulfonate

1-Nicotinoyl-3-phenyl-2-pyrazoline (0.1 g) synthesized in Example 3 was dissolved in ethanol (5 ml). Thereto was added a 1 N methanesulfonic acid ethanol solution (0.6 ml) with ice-cooling. The resulting crystals were collected by filtration, washed with ether and dried to obtain 0.1 g of a title compound as white crystals.

Melting point: 210 to 213° C.

$^1$H-NMR(DMSO-d$_6$), δ ppm: 2.38 (s, 6H), 3.41 (t, 2H), 4.18 (t, 2H), 7.47–7.49 (m, 3H), 7.73–7.77 (m, 2H), 7.86–7.91 (m, 1H), 8.62–8.65 (m, 1H), 8.88–8.90 (m, 1H), 9.22 (s, 1H).

EXAMPLE 6

Synthesis of 1-(2-Pyrazinoyl)-3-phenyl-2-pyrazoline

3-Phenyl-2-pyrazoline was used as a starting material, and the same operation as in Example 2 was conducted to obtain a title compound (yield: 40%).

Melting point: 100 to 103° C.

$^1$H-NMR(CDCl$_3$), δ ppm: 3.2–3.5 (m, 2H), 4.2–4.4 (m, 2H), 7.3–7.5 (m, 3H), 7.5–7.7 (m, 2H), 8.4–8.9 (m, 2H), 8.9–9.1 (m, 1H).

EXAMPLE 7

Synthesis of 1-nicotinoyl-3-(4-fluorophenyl)-2-pyrazoline 3-(4-Fluorophenyl)-2-pyrazoline was used as a starting material, and the same operation as in Example 3 was conducted to obtain a title compound (yield: 50%).

Melting point: 128 to 130° C.

$^1$H-NMR(DMSO-d$_6$), δ ppm: 3.37 (t, 2H), 4.15 (t, 2H), 7.29–7.33 (m, 2H), 7.54–7.57 (m, 1H), 7.75–7.78 (m, 2H), 8.22–8.25 (m, 1H), 8.69–8.71 (m, 1H), 8.99 (d, 1H).

Elemental analysis as $C_{15}H_{12}N_3OF$.

| | |
|---|---|
| Calculated | C: 66.91, H: 4.49, N: 15.60, F: 7.06 |
| Found: | C: 66.89, H: 4.49, N: 15.60, F: 7.06 |

EXAMPLE 8

Synthesis of 1-nicotinoyl-3-(2-fluorophenyl)-2-pyrazoline 3-(2-Fluorophenyl)-2-pyrazoline was used as a starting material, and the same operation as in Example 3 was conducted to obtain a title compound (yield: 50%).

Melting point: 89 to 91° C.

$^1$H-NMR(DMSO-d$_6$), δ ppm: 3.41 (t, 2H), 4.13 (t, 2H), 7.28–7.36 (m, 2H), 7.50–7.56 (m, 2H), 7.74–7.78 (m, 1H), 8.22–8.25 (m, 1H), 8.69–8.70 (m, 1H), 9.03 (d, 1H).

EXAMPLE 9

Synthesis of 1-nicotinoyl-3-(4-bromophenyl)-2-pyrazoline 3-(4-Bromophenyl)-2-pyrazoline was used as a starting material, and the same operation as in Example 3 was conducted to obtain a title compound (yield: 44%).

Melting point: 117 to 119° C.

$^1$H-NMR(CDCl$_3$), δ ppm: 3.3 (t, 2H), 4.3 (t, 2H), 7.3–7.6 (m, 5H), 8.2–8.4 (m, 1H), 8.6–8.8 (m, 1H), 9.2–9.3 (m, 1H).

EXAMPLE 10

Synthesis of 1-nicotinoyl-3-(4-chlorophenyl)-2-pyrazoline 3-(4-Chlorophenyl)-2-pyrazoline was used as a starting material, and the same operation as in Example 3 was conducted to obtain a title compound (yield: 44%).

Melting point: 125 to 126° C.

$^1$H-NMR(CDCl$_3$), δ ppm: 3.23 (t, 2H), 4.2 (t, 2H), 7.3–8.1 (m, 8H), 8.5–8.9 (m, 2H).

Elemental analysis as $C_{13}H_{16}N_2O_3$.

| | |
|---|---|
| Calculated | C: 62.89, H: 6.50, N: 11.28 |
| Found: | C: 62.89, H: 6.88, N: 11.26 |

EXAMPLE 11

Synthesis of 1-nicotinoyl-3-(3-chlorophenyl)-2-pyrazoline 3-(3-Chlorophenyl)-2-pyrazoline was used as a starting material, and the same operation as in Example 3 was conducted to obtain a title compound (yield: 41%).

Melting point: 124 to 126° C.

$^1$H-NMR(CDCl$_3$), δ ppm: 3.24 (t, 2H), 4.24 (t, 2H), 7.2–7.8 (m, 5H), 8.2–8.4 (m, 1H), 8.6–8.7 (m, 1H), 9.2–9.4 (m, 1H).

Elemental analysis as $C_{15}H_{12}N_3OCl$.

| | |
|---|---|
| Calculated | C: 63.05, H: 4.23, N: 14.71, Cl: 12.41 |
| Found: | C: 63.46, H: 4.05, N: 14.78, Cl: 12.14 |

EXAMPLE 12

Synthesis of 1-nicotinoyl-3-(2-chlorophenyl)-2-pyrazoline 3-(2-Chlorophenyl)-2-pyrazoline was used as a starting material, and the same operation as in Example 3 was conducted to obtain a title compound (yield: 18%).

Melting point: 115 to 116° C.

$^1$H-NMR(CDCl$_3$), δ ppm: 3.4 (t, 2H), 4.1 (t, 2H), 7.0–8.0 (m, 8H), 8.3–8.8 (m, 2H).

EXAMPLE 13

Synthesis of 1-nicotinoyl-3-(4-methoxyphenyl)-2-pyrazoline 3-(4-Methoxyphenyl)-2-pyrazoline was used as a starting material, and the same operation as in Example 3 was conducted to obtain a title compound (yield: 42%).

Melting point: 132 to 134° C.

$^1$H-NMR(CDCl$_3$), δ ppm: 3.2 (t, 2H), 3.8 (s, 3H), 4.2 (t, 2H), 6.9–7.7 (m, 4H), 7.3–7.5 (m, 1H), 8.2–8.4 (m, 1H), 8.6–8.7 (m, 1H), 9.2 (m, 1H).

Elemental analysis as $C_{16}H_{15}N_3O_2$.

| | |
|---|---|
| Calculated | C: 68.31, H: 5.37, N: 14.94 |
| Found: | C: 67.78, H: 5.30, N: 14.63 |

EXAMPLE 14

Synthesis of 1-nicotinoyl-3-(2-methoxyphenyl)-2-pyrazoline 3-(2-Methoxyphenyl)-2-pyrazoline was used as a starting material, and the same operation as in Example 3 was conducted to obtain a title -compound (yield: 21%).

Melting point: 130 to 132° C.

$^1$H-NMR(CDCl$_3$), δ ppm: 3.8 (s, 3H), 3.4 (t, 2H), 4.2 (t, 2H), 6.8–7.0 (m, 2H), 7.2–7.5 (m, 2H), 7.6–7.8 (m, 1H), 8.2–8.4 (m, 1H), 8.6–8.7 (m, 1H), 9.2 (m, 1H).

Elemental analysis as C$_{16}$H$_{15}$N$_3$O$_2$.

| | |
|---|---|
| Calculated | C: 68.31, H: 5.37, N: 14.94 |
| Found: | C: 67.86, H: 5.38, N: 14.86 |

EXAMPLE 15

Synthesis of 1-nicotinoyl-3-(2-methoxyphenyl)-4-methyl-2-pyrazoline 3-(2-Methoxyphenyl)-4-methyl-2-pyrazoline was used as a starting material, and the same operation as in Example 3 was conducted to obtain a title compound (yield: 42%).

Melting point: 124 to 125° C.

$^1$H-NMR(CDCl$_3$), δ ppm: 1.2 (d, 3H), 3.9 (s, 3H), 3.8–4.5 (m, 3H), 6.8–7.1 (m, 2H), 7.3–7.8 (m, 3H), 8.3–8.4 (m, 1H), 8.6–8.8 (m, 1H), 9.2–9.3 (m, 1H).

Elemental analysis as C$_{17}$H$_{17}$N$_3$O$_2$.

| | |
|---|---|
| Calculated | C: 69.14, H: 5.80, N: 14.23 |
| Found: | C: 69.06, H: 5.61, N: 14.47 |

EXAMPLE 16

Synthesis of 1-nicotinoyl-3-(2,4-dimethoxyphenyl)-2-pyrazoline 3-(2,4-Dimethoxyphenyl)-2-pyrazoline was used as a starting material, and the same operation as in Example 3 was conducted to obtain a title compound (yield: 43%).

Melting point: 112 to 113° C.

Elemental analysis as C$_{17}$H$_{17}$N$_3$O$_3$.

| | |
|---|---|
| Calculated | C: 65.58, H: 5.50, N: 13.50 |
| Found: | C: 65.38, H: 5.71, N: 13.26 |

EXAMPLE 17

Synthesis of 1-nicotinoyl-3-(4-ethoxyphenyl)-2-pyrazoline 3-(4-Ethoxyphenyl)-2-pyrazoline was used as a starting material, and the same operation as in Example 3 was conducted to obtain a title compound (yield: 35%).

Melting point: 124 to 125° C.

Elemental analysis as C$_{17}$H$_{17}$N$_3$O$_2$.

| | |
|---|---|
| Calculated | C: 69.14, H: 5.80, N: 14.23 |
| Found: | C: 68.99, H: 5.92, N: 14.07 |

EXAMPLE 18

Synthesis of 1-nicotinoyl-3-(2-ethoxyphenyl)-2-pyrazoline 3-(2-Ethoxyphenyl)-2-pyrazoline was used as a starting material, and the same operation as in Example 3 was conducted to obtain a title compound (yield: 51%).

Melting point: 155 to 157° C.

Elemental analysis as C$_{17}$H$_{17}$N$_3$O$_2$.

| | |
|---|---|
| Calculated | C: 69.14, H: 5.80, N: 14.23 |
| Found: | C: 68.54, H: 5.69, N: 14.16 |

EXAMPLE 19

Synthesis of 1-nicotinoyl-3-(4-methylphenyl)-2-pyrazoline 3-(4-Methylphenyl)-2-pyrazoline was used as a starting material, and the same operation as in Example 3 was conducted to obtain a title compound (yield: 25%).

Melting point: 100 to 102° C.

$^1$H-NMR(CDCl$_3$), δ ppm: 2.4 (s, 3H), 3.4 (t, 2H), 4.2 (t, 2H), 7.1–7.6 (m, 4H), 7.2–7.5 (m, 1H), 8.0–8.1 (m, 1H), 8.6–8.7 (m, 1H), 9.2 (m, 1H).

Elemental analysis as C$_{16}$H$_{15}$N$_3$O.

| | |
|---|---|
| Calculated | C: 72.43, H: 5.70, N: 15.84 |
| Found: | C: 72.57, H: 5.65, N: 15.81 |

EXAMPLE 20

Synthesis of 1-nicotinoyl-3-(3-methylphenyl)-2-pyrazoline 3-(3-Methylphenyl)-2-pyrazoline was used as a starting material, and the same operation as in Example 3 was conducted to obtain a title compound (yield: 33%).

Melting point: 99 to 100° C.

Elemental analysis as C$_{16}$H$_{15}$N$_3$O.

| | |
|---|---|
| Calculated | C: 72.43, H: 5.70, N: 15.84 |
| Found: | C: 72.47, H: 5.46, N: 15.92 |

EXAMPLE 21

Synthesis of 1-nicotinoyl-3-(2-methylphenyl)-2-pyrazoline 3-(2-Methylphenyl)-2-pyrazoline was used as a starting material, and the same operation as in Example 3 was conducted to obtain a title compound (yield: 29%).

$^1$H-NMR(CDCl$_3$), δ ppm: 2.5 (s, 3H), 3.3 (t, 2H), 4.2 (t, 2H), 7.2–7.4 (m, 5H), 8.1–8.2 (m, 2H), 8.5–8.6 (m, 1H), 9.2 (m, 1H).

This 1-nicotinoyl-3-(2-methylphenyl)-2-pyrazoline was converted into a hydrochloride thereof using 1 N hydrochloric acid-ethanol.

Melting point: 184 to 186° C.

EXAMPLE 22

Synthesis of 1-nicotinoyl-3-(2,4-dimethylphenyl)-2-pyrazoline 3-(2,4-Dimethylphenyl)-2-pyrazoline was used as a starting material, and the same operation as in Example 3 was conducted to obtain a title compound (yield: 23%).

Melting point: 102 to 104° C.

Elemental analysis as $C_{17}H_{17}N_3O$.

| Calculated | C: 73.10, H: 6.13, N: 15.04 |
|---|---|
| Found: | C: 73.12, H: 6.17, N: 15.08 |

EXAMPLE 23

Synthesis of 1-nicotinoyl-3-(2-trifluoromethylphenyl)-2-pyrazoline 3-(2-trifluoromethylphenyl)-2-pyrazoline was used as a starting material, and the same operation as in Example 3 was conducted to obtain a title compound (yield: 40%).

Melting point: 95 to 97° C.

$^1$H-NMR(DMSO-d$_6$), δ ppm : 3.40 (t, 2H), 4.18 (t, 2H), 7.46–7.49 (m, 1H), 7.69–7.72 (m, 1H), 7.76–7.81 (m, 2H), 7.86 –7.88 (m, 1H), 8.10–8.13 (m, 1H), 8.65–8.66 (m, 1H), 8.91–8.92 (m, 1H).

EXAMPLE 24

Synthesis of 1-nicotinoyl-3-(4-nitrophenyl)-2-pyrazoline 3-(4-Nitrophenyl)-2-pyrazoline was used as a starting material, and the same operation as in Example 3 was conducted to obtain a title compound (yield: 59%).

Melting point: 175 to 177° C.

$^1$H-NMR(CDCl$_3$), δ ppm: 3.3 (t, 2H), 4.4 (t, 2H), 7.2–7.5 (m, 2H), 8.1–8.3 (m, 2H), 8.6–8.8 (m, 1H), 8.6–8.8 (m, 1H), 9.1–9.2 (m, 1H).

Elemental analysis as $C_{15}H_{12}N_4O_3$.

| Calculated | C: 60.81, H: 4.08, N: 18.91 |
|---|---|
| Found: | C: 60.39, H: 3.66, N: 18.86 |

EXAMPLE 25

Synthesis of 1-nicotinoyl-3-(2-nitrophenyl)-2-pyrazoline 3-(2-nitrophenyl)-2-pyrazoline was used as a starting material, and the same operation as in Example 3 was conducted to obtain a title compound (yield: 26%).

Melting point: 123 to 125° C.

Elemental analysis as $C_{15}H_{12}N_4O_3$.

| Calculated | C: 60.81, H: 4.08, N: 18.91 |
|---|---|
| Found: | C: 60.37, H: 3.78, N: 18.71 |

EXAMPLE 26

Synthesis of 2-nicotinoyl-3,3a-dihydro-2H,4H-[1]-benzopyrano[4,3-c]pyrazole

[Reaction 1]

Concentrated hydrochloric acid (0.2 ml) was dropwise added to a solution of 4-chromanone (10 g), dimethylamine hydrochloride (7.1 g) and paraformaldehyde (2.6 g) dissolved in ethanol (20 ml). The mixture was refluxed for 2 hours with heating. The mixture was allowed to cool. The resulting crystals were collected by filtration, washed with acetone and dried to obtain 9 g of β-dimethylaminopropiophenone hydrochloride (yield: 55%).

Melting point: 167 to 169° C.

[Reaction 2]

β-Dimethylaminopropiophenone hydrochloride obtained in Reaction 1 was neutralized with potassium carbonate to obtain β-dimethylaminopropiophenone (6.7 g). This material and hydrazine monohydrate (7.2 g) were refluxed in ethanol (20 ml) for 4 hours with heating. The mixture was allowed to cool and then concentrated. The resulting white crystals were collected by filtration and dissolved in chloroform.

The solution was washed with water, dried and concentrated to obtain 4.5 g of 3,3a-dihydro-2H,4H-[1]-benzopyrano[4,3-c]pyrazole as crystals (yield: 80%).

[Reaction 3]

3,3a-Dihydro-2H,4H-[1]-benzopyrano[4,3-c]pyrazole (4.5 g) obtained in Reaction 2 was used as a starting material, and the same operation as in Example 3 was conducted to obtain 4.4 g of a title compound (yield: 60%).

Melting point: 154–156° C.

This 2-nicotinoyl-3,3a-dihydro-2H,4H-[1]-benzopyrano[4,3-c]pyrazole was converted into a methansulfonate thereof using a 1 N methanesulfonic acid ethanol solution.

Melting point: 233 to 235° C.

$^1$H-NMR(DMSO-d$_6$), δ ppm : 2.38 (s, 3H),3.71–3.92 (m, 1H), 4.19 (t, 1H), 4.41 (t, 1H), 4.73–4.79 (m, 1H), 6.99–7.05 (m, 2H), 7.38–7.44 (m, 1H), 7.63–7.66 (m, 1H), 7.81–7.85 (m, 1H), 8.56–8.59 (m, 1H), 8.85–8.88 (m, 1H), 9.17–9.18 (m, 1H).

EXAMPLE 27

Synthesis of 2-nicotinoyl-6-methoxy-3,3a-dihydro-2H,4H-[1]-benzopyrano[4,3-c]pyrazole 6-Methoxy-3,3a-dihydro-2H,4H-[1]-benzopyrano[4,3-c]pyrazole was used as a starting material, and the same operation as in Example 26 was conducted to obtain a title compound (yield: 32%).

Melting point: 172–173° C.

EXAMPLE 28

Synthesis of 2-nicotinoyl-7-methoxy-3,3a-dihydro-2H,4H-[1]-benzopyrano[4,3-c]pyrazole 7-Methoxy-3,3a-dihydro-2H,4H-[1]-benzopyrano[4,3-c] pyrazole was used as a starting material, and the same operation as in Example 26 was conducted to obtain a title compound (yield: 45%).

Melting point: 145–147° C.

EXAMPLE 29

Synthesis of 2-nicotinoyl-8-methoxy-3,3a-dihydro-2H,4H-[1]-benzopyrano[4,3-c]pyrazole 8-Methoxy-3,3a-dihydro-2H,4H-[1]-benzopyrano[4,3-c] pyrazole was used as a starting material, and the same operation as in Example 26 was conducted to obtain a title compound (yield: 69%).

Melting point: 187–188° C.

EXAMPLE 30

Synthesis of 2-nicotinoyl-6-chloro-3,3a-dihydro-2H,4H-[1]-benzopyrano[4,3-c]pyrazole 6-Chloro-3,3a-dihydro-2H,4H-[1]-benzopyrano[4,3-c] pyrazole was used as a starting material, and the same operation as in Example 26 was conducted to obtain a title compound (yield: 40%).

Melting point: 180–181° C.

$^1$H-NMR(DMSO-d$_6$), δ ppm : 3.77 (t, 1H), 3.87–3.97 (m, 1H), 4.27–4.42 (m, 2H), 4.87–4.91 (m, 1H), 7.03 (t, 1H), 7.52–7.60 (m, 3H), 8.21–8.24 (m, 1H), 8.71–8.72 (m, 1H), 8.99 (d, 1H).

EXAMPLE 31

Synthesis of 2-nicotinoyl-7-chloro-3,3a-dihydro-2H,4H-[1]-benzopyrano[4,3-c]pyrazole 7-Chloro-3,3a-dihydro-2H,4H-[1]-benzopyrano[4,3-c]pyrazole was used as a starting material, and the same operation as in Example 26 was conducted to obtain a title compound (yield: 50%).

Melting point: 175–177° C.

EXAMPLE 32

Synthesis of 2-nicotinoyl-8-chloro-3,3a-dihydro-2H,4H-[1]-benzopyrano[4,3-c]pyrazole 8-Chloro-3,3a-dihydro-2H,4H-[1]-benzopyrano[4,3-c]pyrazole was used as a starting material, and the same operation as in Example 26 was conducted to obtain a title compound (yield: 53%).

Melting point: 165–166° C.

EXAMPLE 33

Synthesis of 2-nicotinoyl-6-methyl-3,3a-dihydro-2H,4H-[1]-benzopyrano[4,3-c]pyrazole 6-Methyl-3,3a-dihydro-2H,4H-[1]-benzopyrano[4,3-c]pyrazole was used as a starting material, and the same operation as in Example 26 was conducted to obtain a title compound (yield: 78%).

Melting point: 144–145° C.

$^1$H-NMR(DMSO-d$_6$), δ ppm: 2.17 (s, 3H), 3.73 (t, 1H), 3.80–3.87 (m, 1H), 4.16–4.22 (m, 1H), 4.35–4.40 (m, 1H), 4.79–4.83 (m, 1H), 6.90–6.93 (m, 1H), 7.27–7.29 (m, 1H), 7.45 (d, 1H), 7.52–7.55 (m, 1H), 8.21–8.24 (m, 1H), 8.70–8.71 (m, 1H).

EXAMPLE 34

Synthesis of 2-nicotinoyl-7-methyl-3,3a-dihydro-2H,4H-[1]-benzopyrano[4,3-c]pyrazole 7-Methyl-3,3a-dihydro-2H,4H-[1]-benzopyrano[4,3-c]pyrazole was used as a starting material, and the same operation as in Example 26 was conducted to obtain a title compound (yield: 39%).

Melting point: 143–145° C.

EXAMPLE 35

Synthesis of 2-nicotinoyl-8-methyl-3,3a-dihydro-2H,4H-[1]-benzopyrano[4,3-c]pyrazole 8-Methyl-3,3a-dihydro-2H,4H-[1]-benzopyrano[4,3-c]pyrazole was used as a starting material, and the same operation as in Example 26 was conducted to obtain a title compound (yield: 63%).

Melting point: 177–178° C.

EXAMPLE 36

Synthesis of 2-(2-pyrazinoyl)-3,3a-dihydro-2H,4H-[1]-benzopyrano-[4,3-c]pyrazole 3,3a-Dihydro-2H,4H-[1]-benzopyrano[4,3-c]pyrazole was used as a starting material, and the same operation as in Example 2 was conducted to obtain a title compound (yield: 53%).

Melting point: 188–190° C.

$^1$H-NMR(DMSO-d$_6$), δ ppm: 3.6–4.5 (m, 1H), 4.6–4.8 (m, 1H), 6.9–7.1 (m, 2H), 7.2–7.5 (m, 2H), 8.8 (s, 2H), 8.9 (s, 1H).

EXAMPLE 37

Synthesis of 2-nicotinoyl-3,3a-dihydro-2H,4H-[1]-benzothiopyrano[4,3-c]pyrazole 3,3a-Dihydro-2H,4H-[1]-benzothiopyrano[4,3-c]pyrazole was used as a starting material, and the same operation as in Example 26 was conducted to obtain a title compound (yield: 70%).

Melting point: 173–175° C.

$^1$H-NMR(DMSO-d$_6$), δ ppm 3.2–4.0 (m, 4H), 4.3–4.6 (m, 1H), 7.0–9.2 (m, 8H).

Elemental analysis as $C_{16}H_{13}N_3OS$.

| Calculated | C: 65.07, H: 4.44, N: 14.23, S: 10.85 |
| Found: | C: 65.51, H: 4.14, N: 14.50, S: 10.71 |

EXAMPLE 38

Synthesis of 2-nicotinoyl-3,3a-dihydrodihydro-2H,4H-[1]-benzothiopyrano[4,3-c]pyrazole-S-oxide To a solution of 2-nicotinoyl-3,3a-dihydro-2H,4H-[1]-benzothiopyrano[4,3-c]pyrazole (6 g) synthesized in Example 37, dissolved in dichloromethane (50 ml) was added m-chloroperbenzoic acid (2.5 g, purity: 70%) with ice-cooling, to give rise to a reaction. After the completion of the reaction, the reaction mixture was washed with a saturated aqueous sodium bicarbonate solution and a saturated aqueous sodium chloride solution. The organic layer was dried and concentrated under vacuum. The residue was purified by silica gel column chromatography (methanol:chloroform=1/40) to obtain 2.3 g of a title compound (yield: 73%).

Melting point: 250° C. (dec.)

Elemental analysis as $C_{16}H_{13}N_3O_2S.0.5H_2O$.

| Calculated | C: 59.98, H: 4.40, N: 13.12, S: 10.01 |
| Found: | C: 59.33, H: 4.11, N: 12.77, S: 10.09 |

EXAMPLE 39

Synthesis of 2-nicotinoyl-3,3a-dihydrodihydro-2H,4H-[1]-benzothiopyrano[4,3-c]pyrazole-S-dioxide 2-Nicotinoyl-3,3a-dihydro-2H,4H-[1]-benzothiopyrano[4,3-c]pyrazole (1.5 g) synthesized in Example 37 was used as a starting material; m-chloroperbenzoic acid (2.5 g, purity: 70%) was used; and the same operation as in Example 38 was conducted to obtain 1 g of a title compound (yield: 61%).

Melting point: 239 to 241° C. (dec.)

Elemental analysis as $C_{16}H_{13}N_3O_3S \cdot 0.5H_2O$.

| | |
|---|---|
| Calculated | C: 57.91, H: 4.25, N: 12.66, S: 9.66 |
| Found: | C: 57.78, H: 3.71, N: 12.36, S: 9.87 |

EXAMPLE 40

Synthesis of 2-(2-pyrazinoyl)-3,3a-dihydro-2H,4H-[1]-benzothiopyrano-[4,3-c]pyrazole 3,3a-Dihydro-2H,4H-[1]-benzothiopyrano[4,3-c]pyrazole was used as a starting material, and the same operation as in Example 36 was conducted to obtain a title compound (yield: 73%).

Melting point: 190–192° C.

$^1$H-NMR(DMSO-$d_6$), δ ppm : 3.2–4.2 (m, 4H), 4.4–4.8 (m, 1H), 7.0–7.4 (m, 3H), 7.6–7.7 (m, 1H), 8.8–9.0 (m, 3H).

Elemental analysis as $C_{15}H_{12}N_4OS$.

| | |
|---|---|
| Calculated | C: 60.80, H: 4.08, N: 18.91, S: 10.82 |
| Found: | C: 60.23, H: 3.64, N: 18.56, S: 10.99 |

EXAMPLE 41

Synthesis of 2-(2-pyrazinoyl)-3,3a-dihydro-2H,4H-[1]-benzothiopyrano-[4,3-c]pyrazole-S-oxide 2-(2-Pyrazinoyl)-3,3a-dihydro-2H,4H-[1]-benzothiopyrano[4,3-c]pyrazole (1.8 g) was used as a starting material, and the same operation as in Example 38 was conducted to obtain a title compound (yield: 41%).

Elemental analysis as $C_{15}H_{12}N_4OS \cdot H_2O$.

| | |
|---|---|
| Calculated | C: 54.54, H: 4.27, N: 16.95, S: 9.70 |
| Found: | C: 54.23, H: 3.97, N: 16.34, S: 9.52 |

EXAMPLE 42

Synthesis of 2-(2-pyrazinoyl)-3,3a-dihydro-2H,4H-[1]-benzothiopyrano-[4,3-c]pyrazole-S-dioxide 2-(2-Pyrazinoyl)-3,3a-dihydro-2H,4H-[1]-benzothiopyrano[4,3-c]pyrazole-S-oxide synthesized in Example 41 was used as a starting material, and the same operation as in Example 39 was conducted to obtain a title compound (yield: 50%).

Melting point: 240 to 242° C.

Elemental analysis as $C_{15}H_{12}N_4O_3S$.

| | |
|---|---|
| Calculated | C: 54.87, H: 3.68, N: 17.06, S: 9.76 |
| Found: | C: 54.62, H: 3.58, N: 16.71, S: 10.02 |

EXAMPLE 43

Synthesis of 2-nicotinoyl-2,3a,4,5-tetrahydronaphtho[1,2-c]pyrazole 2,3a,4,5-Tetrahydronaphtho[1,2-c]pyrazole was used as a starting material and the same operation as in Example 26 was conducted to obtain a title compound (yield: 40%).

Melting point: 141 to 143° C.

This 2-nicotinoyl-2,3a,4,5-tetrahydronaphtho[1,2-c]pyrazole was converted into a methanesulfonate thereof using a 1 N methanesulfonic acid ethanol solution.

Melting point: 207 to 221° C.

$^1$H-NMR(DMSO-$d_6$), δ ppm: 1.80–1.86 (m, 1H), 2.33–2.40 (m, 1H), 2.40 (s, 3H), 2.98–3.07 (m, 2H), 3.56–3.71 (m, 2H), 4.52 (t, 2H), 7.25–7.44 (m, 3H), 7.77 (d, 1H), 7.94–7.99 (m, 1H), 8.73 (d, 1H), 8.91–8.94 (m, 1H), 9.26 (s, 1H).

EXAMPLE 44

Synthesis of 2-(2-pyrazinoyl)-2,3a,4,5-tetrahydronaphtho[1,2-c]pyrazole 2,3a,4,5-Tetrahydronaphtho[1,2-c]pyrazole was used as a starting material and the same operation as in Example 37 was conducted to obtain a title compound (yield: 29%).

Melting point: 184 to 186° C.

EXAMPLE 45

Synthesis of 1-(5-bromonicotinoyl)-3-phenyl-2-pyrazoline 1,1'-Carbonyldiimidazole (1.7 g) was added to a solution of 5-bromonicotinic acid (2 g) dissolved in DMF (20 ml), at room temperature. The mixture was stirred for 1 hour in a nitrogen atmosphere. To the reaction mixture was dropwise added a solution of 3-phenyl-2-pyrazoline (5.7 g) dissolved in DMF (15 ml), with ice-cooling. The mixture was stirred at room temperature for 12 hours. The reaction mixture was concentrated. The residue was dissolved in chloroform. The solution was washed with ice water, dried over anhydrous sodium sulfate, and concentrated. The organic layer was purified by silica gel column chromatography (methanol chloroform=1/100) to obtain 1.4 g of a title compound (yield: 41%).

Melting point: 113 to 115° C.

$^1$H-NMR(CDCl$_3$), δ ppm: 3.31–3.36 (m, 2H), 4.25–4.30 (m, 2H), 7.41–7.48 (m, 3H), 7.70–7.73 (m, 2H), 8.46 (t, 1H), 8.78 (d, 1H), 9.18 (d, 1H).

EXAMPLE 46

Synthesis of 1-(6-methylnicotinoyl)-3-phenyl-2-pyrazoline

6-Methylnicotinic acid was used in place of 5-bromonicotinic acid and the same operation as in Example 45 was conducted to obtain a title compound (yield: 28%).

Melting point: 86 to 87° C.

$^1$H-NMR(CDCl$_3$), δ ppm: 2.64 (s, 3H), 3.28–3.33 (m, 2H), 4.25–4.30 (m, 2H), 7.38–7.40 (m, 1H), 7.40–7.46 (m, 3H), 7.71–7.74 (m, 2H), 8.20–8.22 (m, 1H), 9.20 (d, 1H).

EXAMPLE 47

Synthesis of 1-(3-quinolylcarbonyl)-3-phenyl-2-pyrazoline

3-Quibolinecarboxylic acid was used in place of 5-bromonicotinic acid and the same operation as in Example 45 was conducted to obtain a title compound (yield: 33%).

$^1$H-NMR(CDCl$_3$), δ ppm: 3.37 (t, 2H), 4.35 (t, 2H), 7.41–7.44 (m, 3H), 7.62–8.02 (m, 5H), 8.18 (d, 1H), 8.85 (d, 1H), 9.54 (d, 1H).

Melting point: 107 to 112° C.

Preparation Example 1

Oral Agent Containing, as an Active Ingredient, 1-nicotinoyl-3-phenyl-2-pyrazoline methanesulfonate

EXAMPLE 5

50 g of the above compound of the present invention, 40 g of lactose, 45 g of corn starch and 30 g of crystalline cellulose were mixed thoroughly. The mixture was kneaded with a solution of 5 g of hydroxypropyl cellulose dissolved in water, for granulation. The granules were dried at 50° C. for 4 hours. Thereto was added 3 g of magnesium stearate, followed by thorough mixing. Tablets each weighing 200 mg were formed using a tabletting machine.

Preparation Example 2

Injection Containing, as an Active Ingredient, 1-nicotinoyl-3-phenyl-2-pyrazoline methanesulfonate

EXAMPLE 5

0.5 g of the above compound of the present invention was dissolved in 10 ml of a 0.9% physiological saline solution. The solution was filtered for sterilization and sealed into a 10-ml ampule to obtain an injection.

Test Example 1 Activating Action for Glia Type Glutamic Acid Transporter (GLT-1)

Activating action for GLT-1 was evaluated by a test using COS-7 cells into which rat GLT-1 had been introduced. To COS-7 cells capable of expressing GLT-1 was added a [$^3$H]-glutamate-containing KRH solution (200 µl, final concentration: 2 µM). 3 minutes later, the $^3$H amount was measured using a scintillation counter. A test compound (100 µM) was dissolved in the KRH solution and a treatment was conducted from 1 hour before the addition of [$^3$H]-glutamate. The action of the test compound for intake of glutamic acid was expressed as a percentage relative to the glutamic acid intake ability of solvent-treated group.

Glutamic acid intake (%)=[test compound (dpm)/control (dpm)]×100

This test was conducted based on a method by Shimada et al. [Eur. J. Pharmacol., 386, 263–270 (1990)]. The results of measurement are shown in Table 1.

TABLE 1

Accelerating action for glutamic acid intake

| Test compound: Example No. | Glutamic acid intake (%) |
|---|---|
| 1 | 136 |
| 2 | 126 |
| 5 | 145 |
| 7 | 143 |
| 8 | 134 |
| 9 | 138 |
| 10 | 135 |
| 11 | 140 |
| 12 | 134 |
| 13 | 129 |
| 14 | 124 |
| 15 | 134 |
| 16 | 126 |
| 17 | 129 |
| 19 | 131 |
| 20 | 134 |
| 21 | 129 |
| 23 | 128 |

TABLE 1-continued

Accelerating action for glutamic acid intake

| Test compound: Example No. | Glutamic acid intake (%) |
|---|---|
| 24 | 130 |
| 26 | 131 |
| 31 | 125 |
| 42 | 125 |

Test Example 2 Action for Cerebral Infarct Caused by Middle Cerebral Artery Obstruction in Rat Preparation of rat models having middle cerebral artery obstruction was conducted according to a method of Tamura et al. [J. Cerebral Blood Flow and Metabolism, 53–60 (1981)]. Specifically, 9 to 10 week-old male SD strain rats were used and their left middle cerebral arteries were obstructed under anesthesia by 10% halosen. The compound of Example 5 or 26 was used as a test compound. The compound of Example 5 was intravenously administered in a dosage of 10 mg/kg for 24 hours from right after the obstruction; and the compound of Example 26 was intraperitoneally administered in a dosage of 50 mg/kg right after the obstruction and 6 hours after the obstruction. The brain of each rat was taken out 24 hours after the obstruction of rat middle cerebral artery, was divided into 6 parts, and was dyed with TTC. The section of each dyed part was photographed, and the focus of cerebral infarct was measured using an image analyzer. The rats in control group were as well subjected to middle cerebral artery obstruction. The results are shown in Table 2.

TABLE 2

Action for cerebral infarct reduction using rat models of middle cerebral artery obstruction

| | Number of rats | Focus of cerebral infarct (mm$^3$) |
|---|---|---|
| Control group | 9 | 224.4 ± 71.5 |
| Example 5 | 9 | 131.7 ± 51.6** |
| Control group | 12 | 188.0 ± 54.8 |
| Example 26 | 10 | 135.9 ± 30.5* |

Test Example 3 Toxicity Test

A test compound was administered into ddy mice to investigate its toxicity. The test compound was intraperitoneally administered in a dosage of 100 mg/kg; the mortality rate of the mice 24 hours after the administration was examined; and the toxicity of the test compound was evaluated from the mortality rate. The results are shown in Table 3.

TABLE 3

Results of toxicity test

| Test compound: Example No. | Mortality rate (%) 100 mg/kg (i. p.) |
|---|---|
| 5 | 0 |
| 26 | 0 |

Industrial Applicability

As described above, the compound of the present invention has an action for activating glutamic acid transporter in neurocytes and is useful as a preventive and/or therapeutic agent for cerebral ischemia (cerebral infarct and brain edema), sequela of cerebral ischemia, cephalotrauma, glaucoma, retinopathy, epilepsy and amyotrophic lateral sclerosis (ALS), all caused by glutamic acid toxicity.

What is claimed is:

1. A compound represented by the following formula (1) or a pharmacologically acceptable salt thereof:

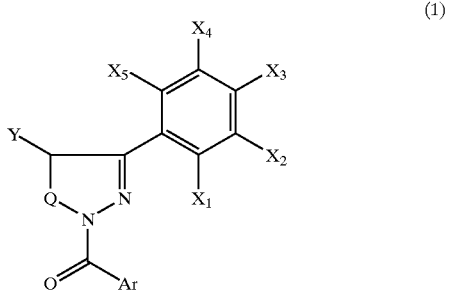

wherein $X_1$, $X_2$, $X_3$, $X_4$, and $X_5$ may be the same or different and are each a hydrogen atom, an alkyl group of 1 to 6 carbon atoms, a trifluoromethyl group, a halogen atom, a nitro group, an alkyloxy group of 1 to 6 carbon atoms, a alkylthio group of 1 to 6 carbon atoms, an alkylsulfinyl group of 1 to 6 carbon atom or an alkylsulfonyl group of 1 to 6 carbon atoms; Y is a hydrogen atom or an alkyl group of 1 to 4 carbon atoms; when $X_5$ is an alkyloxy group, an alkylthio group, an alkylsulfinyl group, an alkylsulfonyl group or an alkyl group, $X_5$ and Y may be bonded to each other to form a 6-membered ring which contains one of O, S, SO or $SO_2$ and where Y is —$CH_2$—; Q is a methylene group or an ethylene group; and Ar is an unsubstituted or Rn-substituted 3-pyridyl group, represented by the following formula:

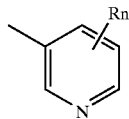

wherein R of Rn is an alkyl group of 1 to 6 carbon atoms or a halogen atom; n is an integer of 0 to 4; and Rn indicates that the number of R is n.

2. A compound or a pharmacologically acceptable salt thereof according to claim 1, wherein Y is a hydrogen atom.

3. A compound or a pharmacologically acceptable salt thereof according to claim 1, wherein Q is a methylene group.

4. A compound or a pharmacologically acceptable salt thereof according to claim 1, wherein Ar is a 3-pyridyl group.

5. A compound or a pharmacologically acceptable salt thereof according to claim 1, wherein $X_5$ is an oxygen atom, Y is a methylene group, and $X_5$ and Y are bonded to each other to form a ring.

6. A compound or a pharmacologically acceptable salt thereof according to claim 4, wherein Y is a hydrogen atom and Q is a methylene group.

7. A compound or a pharmacologically acceptable salt thereof according to claim 5, wherein Ar is a 3-pyridyl group.

8. A process for producing a compound represented by the formula (1) according to claim 1, which comprises reacting a pyrazoline derivative represented by following formula (2):

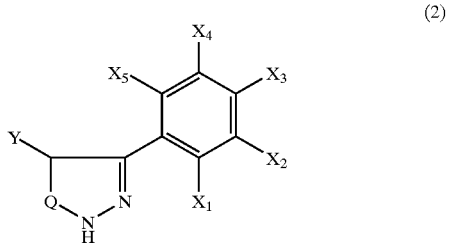

wherein $X_1$, $X_2$, $X_3$, $X_4$, $X_5$, Y and Q have the same definitions as in the formula (1) with a hetero ring derivative represented by the following formula (3):

wherein L is a hydroxyl group or an eliminatable group which can be easily substituted using a nucleophilic reagent: and Ar has the same definition as in the formula (1).

9. A medicinal composition containing, as an active ingredient, a compound or a pharmacologically acceptable salt thereof according to claim 1 and a pharmaceutically acceptable carrier.

* * * * *